(12) United States Patent
Bernotas et al.

(10) Patent No.: US 6,727,246 B2
(45) Date of Patent: Apr. 27, 2004

(54) 1-(AMINOALKYL)-3-SULFONYLINDOLE-AND-INDAZOLE DERIVATIVES AS 5-HYDROXYTRYPTAMINE-6 LIGANDS

(75) Inventors: Ronald Charles Bernotas, Bridgewater, NJ (US); Steven Edward Lenicek, Plainsboro, NJ (US); Schuyler A. Antane, Princeton Junction, NJ (US); Ping Zhou, Plainsboro, NJ (US); Yanfang Li, Lawrenceville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/453,009

(22) Filed: Jun. 3, 2003

(65) Prior Publication Data

US 2003/0232828 A1 Dec. 18, 2003

Related U.S. Application Data

(60) Provisional application No. 60/385,695, filed on Jun. 4, 2002.

(51) Int. Cl.[7] ............... A61K 31/416; A61K 31/5377; A61P 25/28; C07D 231/56; C07D 413/06
(52) U.S. Cl. ............... 514/234.5; 544/140; 544/144; 546/199; 546/201; 548/153; 548/361.5; 548/465; 548/484
(58) Field of Search ................ 544/140, 144; 548/361.5, 153, 484; 514/234.5

(56) References Cited

U.S. PATENT DOCUMENTS

| 4,654,360 A | 3/1987 | Greenhouse et al. |
| 5,132,319 A | 7/1992 | Girard et al. |
| 5,444,056 A | 8/1995 | Gubin et al. |
| 6,187,805 B1 | 2/2001 | McAllister et al. |
| 6,251,923 B1 | 6/2001 | Höfgen et al. |

FOREIGN PATENT DOCUMENTS

| WO | WO 01/82909 A2 | 11/2001 |

OTHER PUBLICATIONS

Garcia, J. et al., Tetrahedron Letters, 1985, 26(15):1827–1830.
Cuadro, A. M. et al., Synthetic Communications, 1991, 21(4):535–544.
Wojciechowski, K. and Makosza, M., Synthesis, 1986, 651–653.
Takahashi, M. and Suga, D., Synthesis, 1998, 986–990.

*Primary Examiner*—Robert W. Ramsuer
(74) *Attorney, Agent, or Firm*—Barbara L. Lences

(57) ABSTRACT

The present invention provides compounds of formula I and the use thereof for the treatment of central nervous system disorders related to or affected by the 5-HT6 receptor.

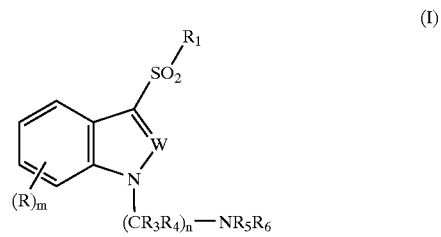

20 Claims, No Drawings

1-(AMINOALKYL)-3-SULFONYLINDOLE- AND -INDAZOLE DERIVATIVES AS 5-HYDROXYTRYPTAMINE-6 LIGANDS

BACKGROUND OF THE INVENTION

This application claims priority from copending provisional application Serial No. 60/385,695, filed Jun. 4, 2002, the entire disclosure of which is hereby incorporated by reference.

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320–327) and subsequently in human tissue (Kohen, R.; Metcalf, M. A.; Khan, N.; Druck, T.; Huebner, K.; Sibley, D. R. *Journal of Neurochemistry* 1996, 66, 47–56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268–276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64,1105–1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research*, 1997, 746, 207–219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Jornal of Pharmacology*, 1999, 126(7), 1537–1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23–26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901–5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonis at this site (Branchek, T. A.; Blackburn, T. P. *Annual Reviews in Pharmacology and Toxicology* 2000, 40, 319–334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606–1612).

Taken together, the above studies strongly suggest that compounds which are 5-HT6 receptor ligands may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a 1-(aminoalkyl)-3-sulfonylindole or -indazole of formula I

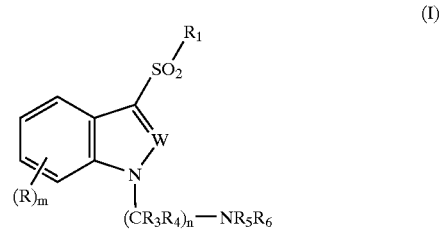

wherein
W is N or $CR_2$;
R is H, halogen, CN, $OCO_2R_7$, $CO_2R_8$, $CONR_9R_{10}$, $SO_pR_{11}$, $NR_{12}R_{13}$, $OR_{14}$, $COR_{15}$ or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_5$ and $R_6$ may be taken together with the atom to which they are attached to form an optionally substituted 5- to 8-membered ring optionally containing an additional heteroatom selected from O, $NR_{16}$ or $SO_x$;
m is 0 or an integer of 1, 2 or 3;
n is an integer of 2, 3, 4 or 5;
p and x are each independently 0 or an integer of 1 or 2;
$R_7$, $R_8$, $R_{11}$, $R_{15}$ and $R_{16}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_9$ and $R_{10}$ are each independently H or a $C_1$–$C_6$alkyl or $C_3$–$C_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;
$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;
$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
q is 0 or an integer of 1 or 2; and
$R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted; or
a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that 1-(aminoalkyl)-3-sulfonylindole and -indazole derivatives of formula I demonstrate 5-HT6 affinity. Advantageously, said indole and indazole derivatives may be used as effective therapeutic agents for the treatment of central nervous system (CNS) disorders associated with or affected by the 5-HT6 receptor. Accordingly, the present invention provides 1-(aminoalkyl)-3-sulfonylindole and -indazole derivatives of formula I

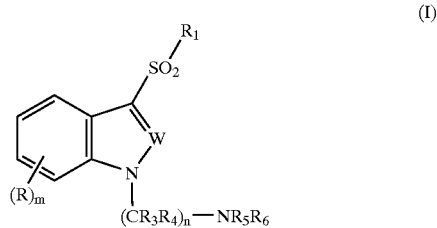

wherein
W is N or $CR_2$;
R is H, halogen, CN, $OCO_2R_7$, $CO_2R_8$, $CONR_9R_{10}$, $SO_pR_{11}$, $NR_{12}R_{13}$, $OR_{14}$, $COR_{15}$ or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;
$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
$R_2$ is H, halogen, or a $C_1$–$C_6$alkyl, $C_1$–$C_6$alkoxy, $C_3$–$C_7$cycloalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_5$ and $R_6$ may be taken together with the atom to which they are attached to form an optionally substituted 5- to 8-membered ring optionally containing an additional heteroatom selected from O, $NR_{16}$ or $SO_x$;
m is 0 or an integer of 1, 2 or 3;
n is an integer of 2, 3, 4 or 5;
p and x are each independently 0 or an integer of 1 or 2;
$R_7$, $R_8$, $R_{11}$, $R_{15}$ and $R_{16}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or a $C_1$–$C_6$alkyl or $C_3$–$C_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;

$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;

$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

q is 0 or an integer of 1 or 2; and $R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted; or a stereoisomer thereof or a pharmaceutically acceptable salt thereof.

As used in the specification and claims, the term halogen designates F, Cl, Br or I and the term cycloheteroalkyl designates a 5- to 7-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR', O or S; and R' is H or an optional substituent as described hereinbelow:

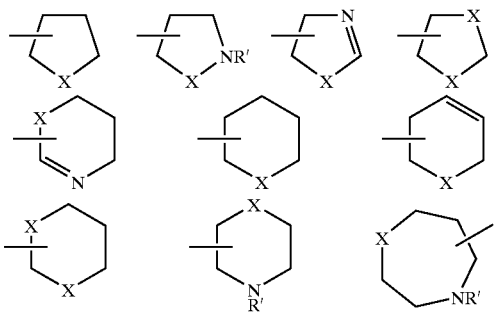

Similarly, as used in the specification and claims, the term heteroaryl designates a 5- to 10-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system e.g., having 6 to 14 carbon atoms such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

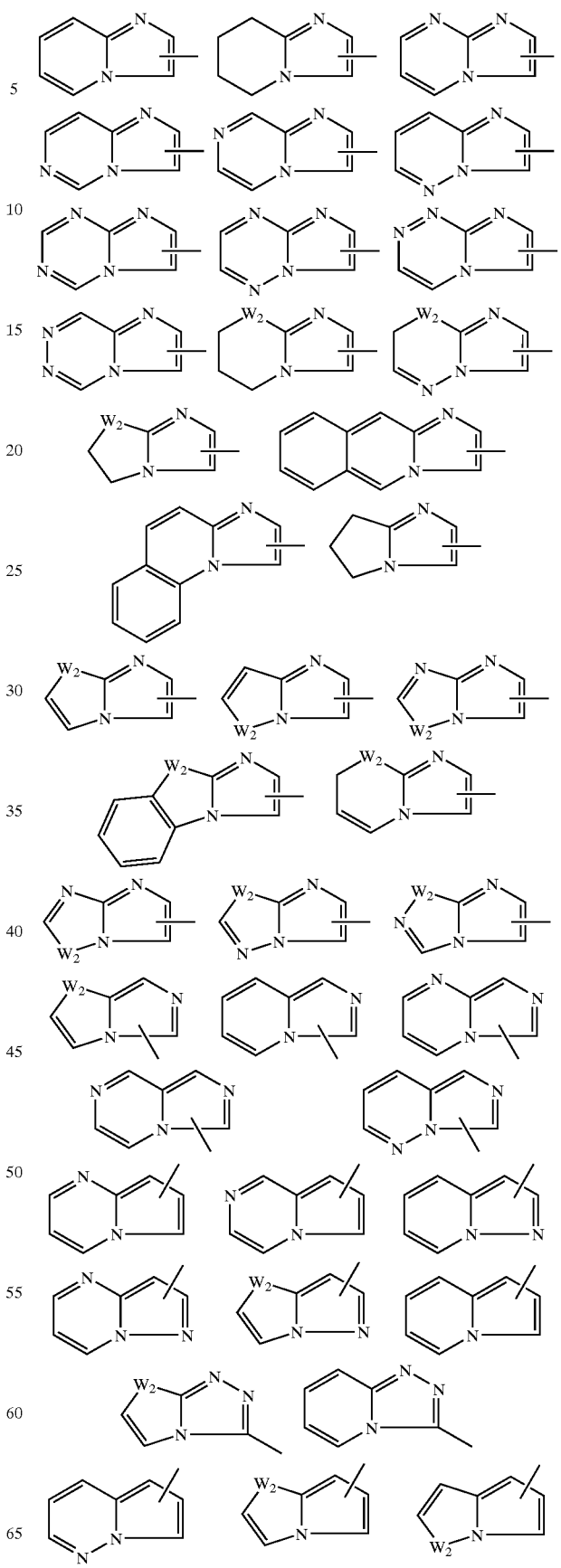

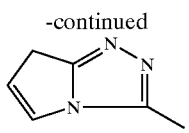

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl (such as heteroaryl or cycloheteroalkyl) or cycloalkyl groups, preferably halogen atoms or lower (e.g. $C_1$–$C_6$) alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein n is 2. Also preferred are those compounds of formula I wherein $R_1$ is an optionally substituted phenyl, naphthyl or imidazothiazolyl group. Another group of preferred compounds of formula I are those compounds wherein $R_3$ and $R_4$ are H.

More preferred compounds of the invention are those formula I compounds wherein n is 2 and $R_2$ is H or $CH_3$.

Another group of more preferred compounds are those compounds of formula I wherein n is 2 and $R_5$ and $R_6$ are each independently H or $C_1$–$C_4$alkyl. Further more preferred formula I compounds are those compounds wherein n is 2; R is H, halogen or $C_1$–$C_4$alkoxy; $R_1$ is an optionally substituted phenyl, naphthyl or imidazothiazolyl group; and $R_3$ and $R_4$ are H.

Examples of preferred compounds of the invention include:

2-[5-methoxy-3-(phenylsulfonyl)-1H-indol-1-yl]ethylamine;

6-chloro-1-(3-morpholin-4-yl-propyl)-3-(phenylsulfonyl)-1H-indole;

5-methoxy-3-(phenylsulfonyl)-1-(3-pyrrolidin-1-yl-propyl)-1H-indole;

N,N-dimethyl-N-{3-[3-(4-fluorophenylsulfonyl)-5-methoxy-1H-indol-1-yl]-propyl}-amine;

N,N-dibenzyl-N-{[2-(3-phenylsulfonyl)-1H-indol-1-yl]ethyl}amine;

5-methoxy-3-(phenylsulfonyl)-1-(2-pyrrolidin-1-yl-ethyl)-1H-indole;

N,N-dimethyl-N-{2-[3-(4-fluorophenylsulfonyl)-5-methoxy-1H-indol-1-yl]-ethyl}amine;

N,N-dimethyl-3-[3-(phenylsulfonyl)-1H-indol-1-yl]propan-1-amine;

2-[3-(phenylsulfonyl)-1H-indol-1-yl]ethylamine;

2-[3-(naphth-1-ylsulfonyl)-1H-indol-1-yl]ethylamine;

2-{3-[(6-chloro-imidazo[2,1-b][1,3]thiazol-5-yl)lsulfonyl]-1H-indol-1-yl]ethylamine;

3-[3-(phenylsulfonyl)-1H-indol-1-yl]propan-1-amine;

3-[3-(4-fluorophenylsulfonyl)-5-methoxy-1H-indol-1-yl]propan-1-amine;

3-(phenylsulfonyl)-1-(2-piperidin-1-yl-ethyl)-1H-indole;

3-[5-methoxy-3-(phenylsulfonyl)-1H-indol-1-yl]propan-1-amine;

3-[6-chloro-3-(phenylsulfonyl)-1H-indol-1-yl]propan-1-amine;

6-chloro-1-(2-morpholin-4-yl-ethyl)-3-(phenylsulfonyl)-1H-indole;

3-(phenylsulfonyl)-1-(3-piperidin-1-yl-propyl)-1H-indole;

2-[6-chloro-3-(phenylsulfonyl)-1H-indol-1-yl]ethylamine;

2-[3-(4-fluorophenylsulfonyl)-5-methoxy-1H-indol-1-yl]ethylamine;

N,N-dimethyl-N-{2-[2-methyl-3-(phenylsulfonyl)-1H-indol-1-yl]ethyl}amine;

N,N-dimethyl-N-{2-[5-carbonitrile-3-(phenylsulfonyl)-1H-indol-1-yl]ethyl}amine hydrochloride;

N,N-dimethyl-N-{2-[4-fluoro-3-(phenylsulfonyl)-1H-indol-1-yl]ethyl}amine;

N,N-dimethyl-N-{2-[7-chloro-3-(phenylsulfonyl)-1H-indol-1-yl]-ethyl}amine;

N,N-dimethyl-N-{2-[4-chloro-3-(phenylsulfonyl)-1H-indol-1-yl]-ethyl}amine;

N,N-dimethyl-N-{2-[4-methyl-3-(phenylsulfonyl)-1H-indol-1-yl]ethyl}amine;

N,N-dimethyl-N-{2-[7-ethyl-3-(phenylsulfonyl)-1H-indol-1-yl]ethyl}amine;

N,N-dimethyl-{N-[3-(thien-2ylsulfonyl)-1H-indol-1-yl]ethyl}amine;

2-[3-(thien-2-ylsulfonyl)-1H-indol-1-yl]ethylamine;

1-[2-(dimethylamino)ethyl]-3-(phenylsulfonyl)-1H-indole-5-carbonitrile;
1-[2-(dimethylamino)ethyl]-3-(phenylsulfonyl)-1H-indole-7-carbonitrile;
2-[5-methoxy-3-(phenylsulfonyl)-1H-indazol-1-yl)]ethylamine;
6-chloro-1-(3-morpholin-4-yl-propyl)-3-(phenylsulfonyl)-1H-indazole;
5-methoxy-3-(phenylsulfonyl)-1-(3-pyrrolidin-1-yl-propyl)-1H-indazole;
N,N-dimethyl-N-{3-[3-(4-fluorophenylsulfonyl)-5-methoxy-1H-indazol-1-yl]-propyl}-amine;
N,N-dibenzyl-N-{[2-(3-phenylsulfonyl)-1H-indazol-1-yl]ethyl}amine;
5-methoxy-3-(phenylsulfonyl)-1-(2-pyrrolidin-1-yl-ethyl)-1H-indazole;
N,N-dimethyl-N-3-{2-[3-(4-fluorophenylsulfonyl)-5-methoxy-indazol-1-yl]-ethyl}amine;
N,N-dimethyl-N-3-[3-(phenylsulfonyl)-1H-indazol-1-yl]propan-1-amine;
2-[3-(phenylsulfonyl)-1H-indazol-1-yl]ethylamine;
2-[3-(naphth-1-ylsulfonyl)-1H-indazol-1-yl]ethylamine;
2-{3-[(6-chloro-imidazo[2,1-b][1,3]thiazol-5-yl)lsulfonyl]-1H-indazol-1-yl]ethylamine;
3-[3-(phenylsulfonyl)-1H-indazol-1-yl]propan-1-amine;
3-[3-(4-fluorophenylsulfonyl)-5-methoxy-indazol-1-yl]propan-1-amine;
3-(phenylsulfonyl)-1-(2-piperidin-1-yl-ethyl)-1H-indazole;
3-[5-methoxy-3-(phenylsulfonyl)-1H-indazol-1-yl]propan-1-amine;
3-[6-chloro-3-(phenylsulfonyl)-1H-indazol-1-yl]propan-1-amine;
6-chloro-1-(2-morpholin-4-yl-ethyl)-3-(phenylsulfonyl)-1H-indazole;
3-(phenylsulfonyl)-1-(3-piperidin-1-yl-propyl)-1H-indazole;
2-[6-chloro-3-(phenylsulfonyl)-1H-indazol-1-yl]ethylamine;
2-[3-(4-fluorophenylsulfonyl)-5-methoxy-1H-indazol-1-yl]ethylamine;
N,N-dimethyl-N-{2-[2-methyl-3-(phenylsulfonyl)-1H-indazol-1-yl]ethyl}-amine;
N,N-dimethyl-N-{2-[2-methyl-3-(naphth-1-ylsulfonyl)-1H-indazol-1-yl]ethyl}-amine;
N,N-dimethyl-N-{2-[5-carbonitrile-3-(phenylsulfonyl)-1H-indazol-1-yl]ethyl}amine;
N,N-dimethyl-N-{2-[4-fluoro-3-(phenylsulfonyl)-1H-indazol-1-yl]ethyl}amine;
N,N-dimethyl-N-{2-[3-(naphth-1-ylsulfonyl)-1H-indazol-1-yl]ethyl}amine;
N,N-dimethyl-N-{2-{[3-(6-chloro-imidazo[1,2-b][1,3]thiazol-5-yl)sulfonyl]-1H-indazol-1-yl}ethyl}amine;
N,N-dimethyl-N-{2-[7-chloro-3-(phenylsulfonyl)-1H-indazol-1-yl]-ethyl}amine;
N,N-dimethyl-N-{2-[4-chloro-3-(phenylsulfonyl)-1H-indazol-1-yl]-ethyl}amine;
N,N-dimethyl-N-{2-[4-methyl-3-(phenylsulfonyl)-1H-indazol-1-yl]ethyl}-amine;
the stereoisomers thereof; or the pharmaceutically acceptable salts thereof.

Advantageously, the present invention provides a process for the preparation of a compound of formula I which comprises reacting a compound of formula II with a haloalkylamine of formula III in the presence of a base optionally in the presence of a solvent. The process of the invention is shown in flow diagram I wherein Hal represents Cl, Br or I.

Flow Diagram I

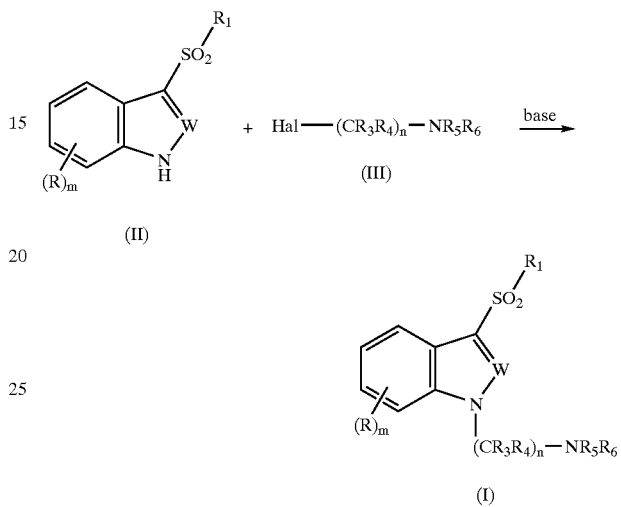

Bases suitable for use in the process of the invention include strong bases such as NaH, KOt-Bu, NaOH or any conventional base capable of removing a proton from a basic indole or indazole nitrogen atom.

Solvents suitable for use in the process of the invention include one or more polar solvents such as dimethyl formamide, dimethylsulfoxide, acetonitrile, tetrahydrofuran, water or the like. If two immiscible solvents are used, a phase transfer catalyst may be present. Preferably, for the preparation of those compounds of formula I wherein $R_5$ and $R_6$ are H, the compound of formula II may be reacted with a base as described hereinabove in the presence of a phase transfer catalyst, such as tetrabutylammonium hydrogensulfate, to give the desired compound of formula I wherein $R_5$ and $R_6$ are H.

Compounds of formula I may also be prepared by reacting the formula II compound with a di-haloalkyl compound of formula IV to give the 1-(haloalkyl)indole or -indazole or formula V and reacting the formula V compound with an amine, $HNR_5R_6$, optionally in the presence of a base to give the desired formula I product. The reaction is shown in flow diagram II wherein Hal is Cl, Br or I.

Flow Diagram II

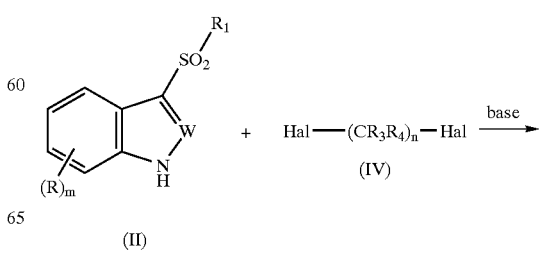

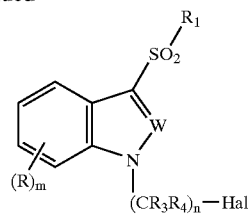

(V)

↓ HNR₅R₆

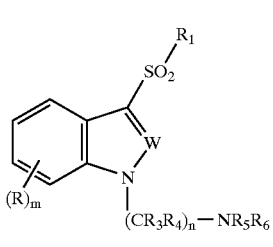

(I)

Compounds of formula II may be prepared using conventional synthetic methods and, if required, standard separation and isolation techniques. For example, for compounds of formula II wherein W is CR₂ (IIa), a nitrobenzene compound of formula VI may be reacted with a chloromethylsulfonyl compound of formula VII in the presence of a strong base to give the intermediate of formula VII; said formula VII intermediate may then be treated with a reducing agent such as Fe, Zn or Sn in the presence of an acid to give the amine of formula IX; said amine may then be reacted with the appropriate orthoester of formula X to give the formula XI compound; and said formula XI compound may be cyclized in the presence of a base to give the desired formula IIa 3-sulfonylindole. The general synthetic method is described by W. Wojciechowski and M. Makosza, *Synthesis* 1986, 651–653. Similarly, the formula IX amine may be reacted with NaNO₂ in the presence of an acid to give those indazole compounds of formula II wherein W is N (IIb). The reaction sequences are shown in flow diagram III.

Flow Diagram III

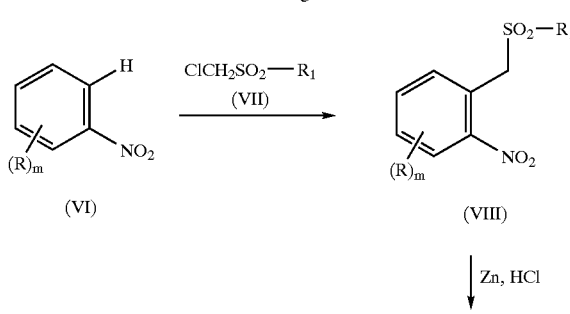

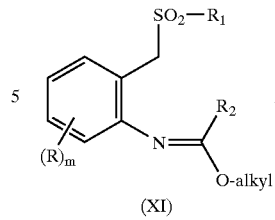 ← R₂C(O-alkyl)₃ (X) — 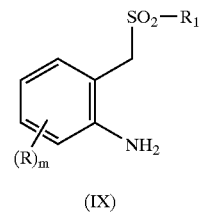

(XI)  (IX)

↓ base    ↓ NaNO₂, HCl

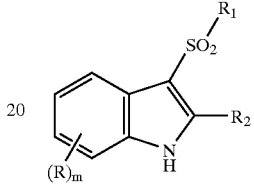  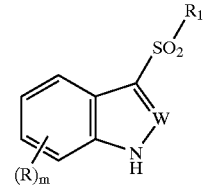

(IIa)  (IIb)

Compounds of formula II may also be prepared directly from an indole or indazole of formula XII by reacting the formula XII substrate with iodine to give the 3-iodoindole or -indazole of formula XIII; coupling the formula XIII compound with an appropriate thiol of formula XIV to give the 3-thioindole or -indazole of formula XV and oxidizing said formula XV compound with a conventional oxidizing agent such as H₂O₂, m-chloroperbenzoic acid, or the like to afford the desired formula II intermediate. The reaction is shown in flow diagram IV.

Flow Diagram IV

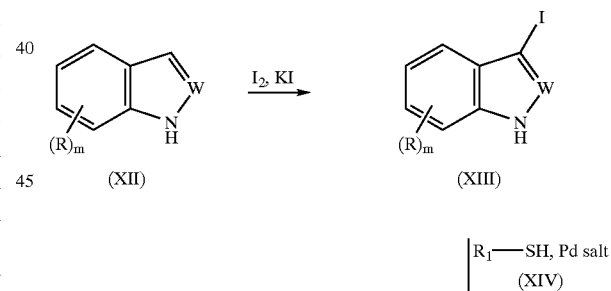

Alternatively, the formula XV 3-thioindole or -indazole compound may be prepared in a single step from the formula XII substrate by reacting the formula XII compound with the formula XIV thiol in the presence of iodine, preferably in a polar solvent such as aqueous alcohol. The thus-obtained formula XV compounds may then be oxidized as shown hereinabove to give the formula II intermediate. The thus-obtained formula II intermediate may then be carried on to the desired compounds of formula I via the alkylation of the basic indole or indazole nitrogen atom as shown in flow diagrams I and II hereinabove.

Compounds of formula XII may also be converted to the desired compounds of formula I wherein $R_5$ and $R_6$ are other than H (Ia) by reacting the formula XII compound with an amine of formula IIIa wherein $R_5$ and $R_6$ are other than H to give the N-alkylated compound of formula XVI; reacting the formula XVI compound with a sulfonyl chloride of formula XVII, optionally in the presence of a catalyst such as $Ag(OSO_2CF_3)$ or $Bi(OSO_2CF_3)_3$, to give the desired compound of formula Ia. Similarly, compounds of formula I wherein $R_5$ and $R_6$ are H (Ib) may be prepared directly from the formula XII intermediate by reacting said formula XII intermediate with a nitrile of formula XVIII to give the corresponding alkylated compound of formula XIX; sulfonylating said formula XIX compound to give the compound of formula XX; and reducing the formula XX compound using conventional reducing reagents such as borane in tetrahydrofuran (THF) to give the desired compounds of formula Ib. The reactions are shown in flow diagram V wherein Hal represents Cl, Br or I.

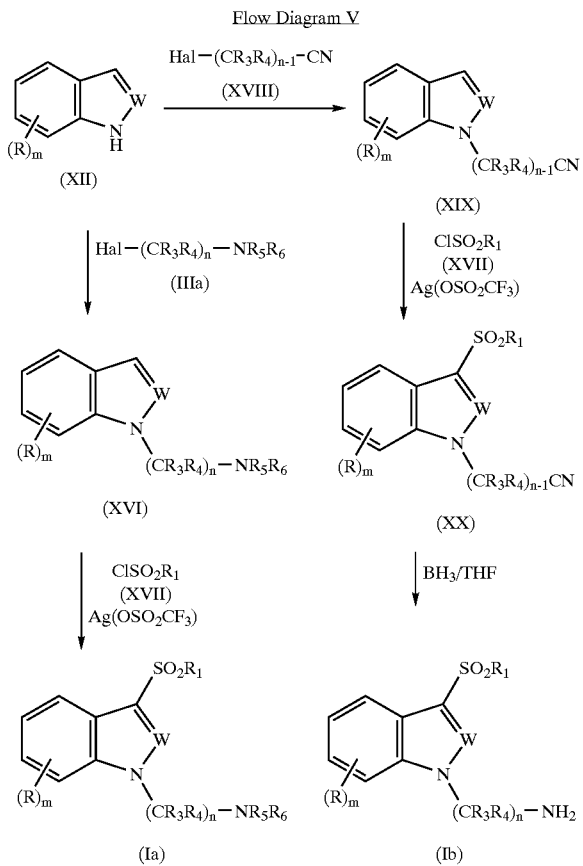

Advantageously, the formula I compounds of the invention are useful for the treatment of CNS disorders relating to or affected by the 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula 1. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms EtOAc, THF and DMF designate ethyl acetate, tetrahydrofuran and dimethyl formamide, respectively. All chromatography is performed using $SiO_2$ as support.

EXAMPLE 1

Preparation of 3-(Phenylthio)-1H-indole

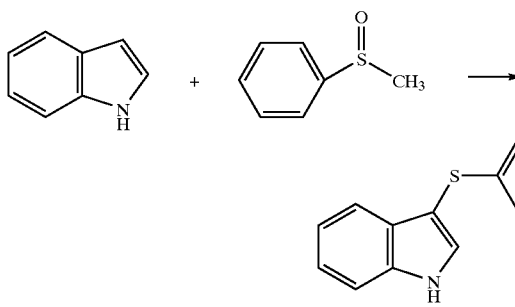

A solution of methyl phenyl sulfoxide (4.0 g, 147 mmol) in $CH_2Cl_2$ is cooled to −78° C., treated dropwise with trifluoroacetic anhydride (4.0 mL, 5.99 g, 28.5 mmol), stirred for 30 min at −78° C., treated with a solution of indole (1.82 g, 15.6 mmol) in $CH_2Cl_2$, stirred for 30 min at −78° C., treated with triethylamine (20 mL, 145 mmol), stirred for 4 days at ambient temperatures and diluted with water. The phases are separated. The organic phase is dried over $MgSO_4$ and concentrated in vacuo. The resultant residue is chromatographed (1:99 methanol:$CH_2Cl_2$) to give the title product as a white solid, 3.08 g (88% yield), mp 149–151° C., characterized by mass spectral and HNMR analyses.

EXAMPLE 2

Preparation of 3-(Phenylsulfonyl)-1H-indole

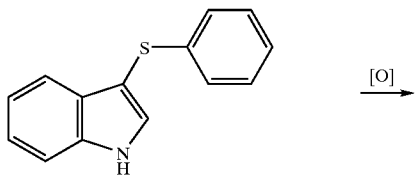

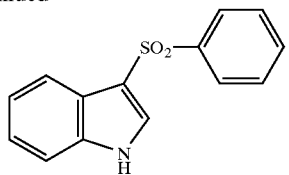

A stirred solution of 3-(phenylthio)-1H-indole (12.0 g, 53.3 mmol) in $CH_2Cl_2$ (800 mL) is chilled to 0° C., treated with 3-chloroperbenzoic acid (20.2 g, 117 mmol) and stirred for 4 h at ambient temperature. The reaction is washed sequentially with water and saturated $NaHCO_3$, dried over $MgSO_4$ and concentrated in vacuo. Chromatography (1:49 methanol:$CH_2Cl_2$) of the resultant residue affords the title compound as a white solid, 9.83 g (72% yield), mp 149–151° C., characterized by mass spectral and HNMR analyses.

EXAMPLE 3

Preparation of N,N-Dimethyl-N-{2-[3-(phenylsulfonyl)-1H-indol-1-yl] ethyl}amine Hydrochloride

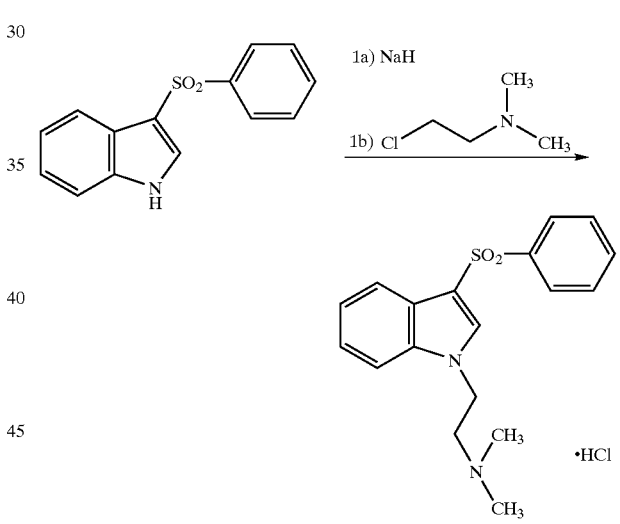

A stirred solution of 3-(phenylsulfonyl)-1H-indole (250 mg, 0.97 mmol) in anhydrous DMF is chilled to 0° C., treated with 60% NaH in mineral oil (117 mg, 2.91 mmol), stirred for 2 h at ambient temperature, cooled to −20° C., treated with 2-(dimethylamino)ethylchloride hydrochloride (210 mg, 1.46 mmol), stirred for 16 h at 60° C., quenched with water and extracted with $CH_2Cl_2$. The combined extracts are dried over $MgSO_4$ and concentrated in vacuo to a semi-solid. The semi-solid is crystallized from $CH_2Cl_2$/hexane to give the free amine as a white solid (205 mg, 64% yield). The solid is dissolved in ethanol, treated with 4N HCl in dioxane and concentrated in vacuo. The resultant residue is crystallized from ethanol/ether to afford the title compound as a white solid, 188 mg, mp: 95–98° C., characterized by mass spectral and HNMR analyses.

EXAMPLE 4

Preparation of 2-{3-[3-(Phenylsulfonyl)-1H-indol-1-yl]propyl}isoindole-1,3-dione

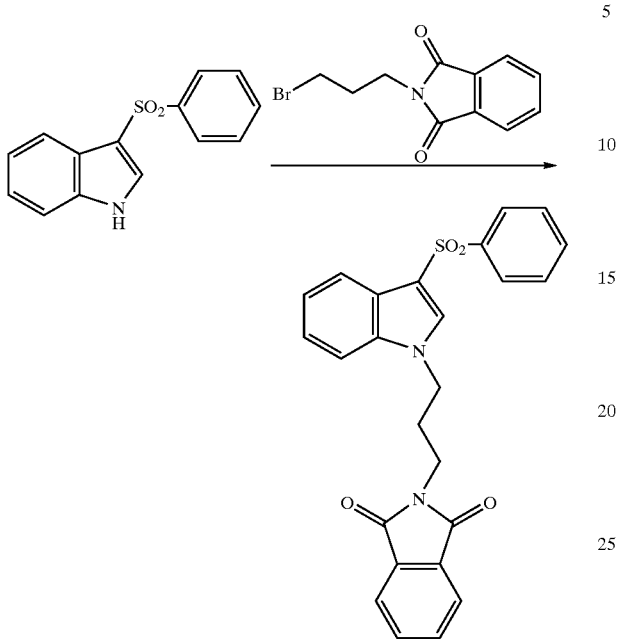

A stirred solution of 3-(phenylsulfonyl)-1H-indole (600 mg, 2.33 mmol) in anhydrous DMF is chilled to 0° C., treated with 60% NaH in mineral oil (140 mg, 3.50 mmol), stirred for 2 h at ambient temperature, treated with N-(3-bromopropyl)-phthalimide (751 mg, 2.80 mmol), stirred for 16 h at ambient temperature, quenched with water and extracted with $CH_2Cl_2$. The combined organic extracts are dried over $MgSO_4$ and concentrated in vacuo to a semi-solid. Chromatography (1:99 methanol:$CH_2Cl_2$) of the semi-solid affords the title compound as a white solid, 427 mg (41% yield), mp 205–206° C., characterized by mass spectral and HNMR analyses.

EXAMPLE 5

Preparation of 3-[3-(Phenylsulfonyl)-1H-indol-1-yl]propan-1-amine Hydrochloride

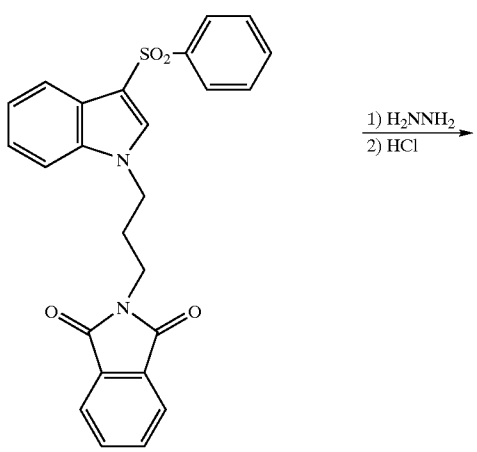

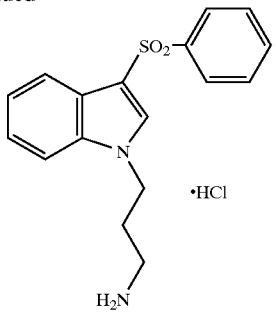

A stirred solution of 2-{3-[3-(phenylsulfonyl)-1H-indol-1-yl]-propyl}-isoindole-1,3-dione (350 mg, 0.79 mmol) and anhydrous hydrazine (0.30 mL, 330 mg, 10.3 mmol) in ethanol is heated at reflux temperature for 16 h and concentrated in vacuo. The resultant residue is treated with 1 N NaOH and extracted with $CH_2Cl_2$. The combined extracts are washed sequentially with water and saturated NaCl, dried over $MgSO_4$ and concentrated in vacuo. Chromatography (3:97 methanol:$CH_2Cl_2$) of the residue affords a white solid (135 mg, 54%). The solid is dissolved in ethanol, treated with 4N HCl in dioxane and concentrated in vacuo. This residue is crystallized in ethanol/ether to give the title compound as a white solid, 134 mg, mp 135–137° C., characterized by mass spectral and HNMR analyses.

EXAMPLE 6–15

Preparation of 1-(Aminoalkyl)-3-(phenylsulfonyl)-1H-indole Derivatives

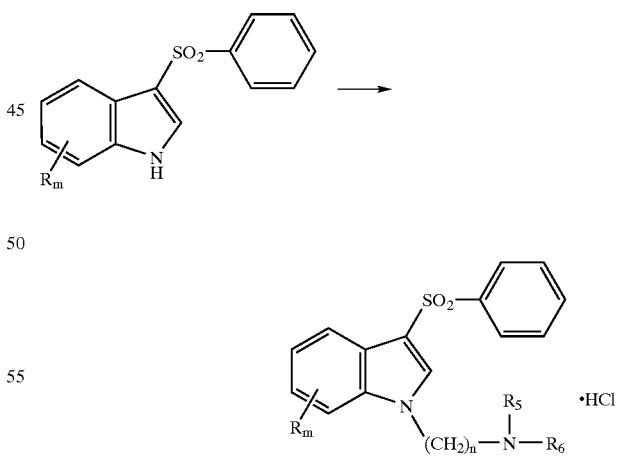

Using essentially the same procedures described in Examples 1–5 hereinabove and employing the appropriately substituted indole substrate and desired amine, the compounds shown in Table I are obtained and identified by mass spectral and HNMR analyses.

TABLE I

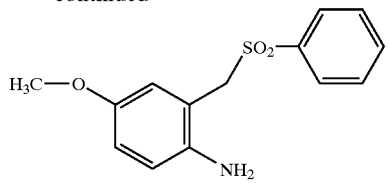

| Ex. No. | Rm | n | R5 | R6 | mp °C. | % Yield |
|---|---|---|---|---|---|---|
| 6 | H | 2 | CH₂C₆H₅ | CH₂C₆H₅ | 222–225 | 78[a] |
| 7 | H | 4 | CH₃ | CH₃ | 184–187 | 72[a] |
| 8 | 5-CN | 2 | CH₃ | CH₃ | 280 (dec) | 89[a] |
| 9 | 4-F | 2 | CH₃ | CH₃ | 201–203 | 74 |
| 10 | 7-Cl | 2 | CH₃ | CH₃ | 240–242 | 81 |
| 11 | 4-Cl | 2 | CH₃ | CH₃ | 209–211 | 62 |
| 12 | 4-CH₃ | 2 | CH₃ | CH₃ | 220–221 | 42 |
| 13 | 7-C₂H₅ | 2 | CH₃ | CH₃ | 213–216 | 59 |
| 14 | 7-CN | 2 | CH₃ | CH₃ | 134–136 | 30 |
| 15 | H | 3 | CH₃ | CH₃ | 207–209 | 64[a] |

[a]Free amine

EXAMPLE 16

Preparation of 4-Methoxy-1-nitro-2-[(phenylsulfonyl)methyl]benzene

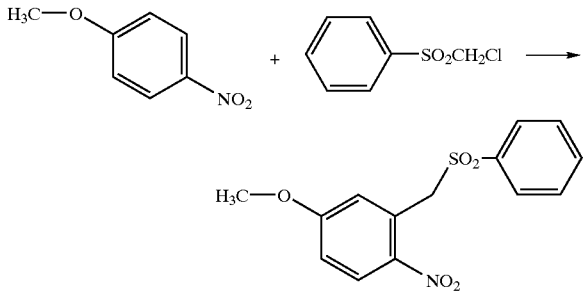

A solution of 4-nitroanisole (3.83 g, 25.0 mmol) and chloromethyl-phenylsulfone (4.76 g, 25.0 mmol) in dry THF is cooled to −60° C., treated with 1.0M KOt-Bu in THF (55.0 mL, 55.0 mmol), allowed to warm to −20° C. over 1 h, treated with glacial acetic acid, warmed to 20° C., treated with water and extracted with CH₂Cl₂. The combined extracts are dried over MgSO₄ and concentrated in vacuo. The resulting solid is triturated with 25:75 ethyl acetate:hexanes and filtered. The filtercake is dried in vacuo to give the title product as a light tan solid, 7.05 g (92% yield), mp 167–169° C., characterized by mass spectral and HNMR analyses.

EXAMPLE 17

Preparation of 4-Methoxy-2-[(phenylsulfonyl)methyl]aniline

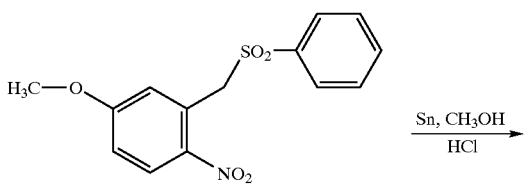

A stirred mixture of 4-methoxy-1-nitro-2-[(phenylsulfonyl)methyl]benzene (6.14 g, 20.0 mmol), and granular tin (10.4 g, 88 mmol) in methanol and concentrated hydrochloric acid (60 mL) is heated under nitrogen at 45° C. for 6 h. The reaction mixture is poured onto NaHCO₃ while stirred, water is added and the mixture is extracted with ethyl acetate. The combined extracts are dried over MgSO₄ and concentrated in vacuo to afford the title product as an off-white solid, 5.39 g (97% yield), mp 110–111° C., characterized by mass spectral and HNMR analyses.

EXAMPLE 18

Preparation of 5-Methoxy-3-(phenylsulfonyl)-1H-indole

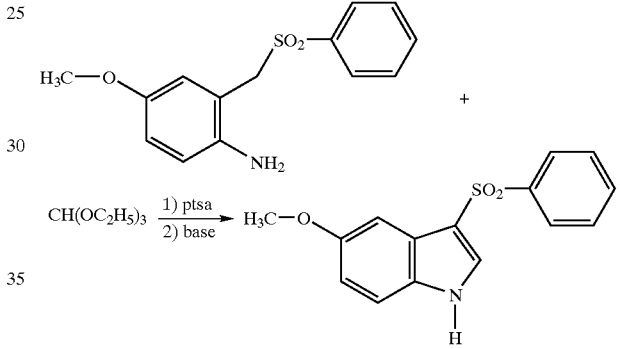

A stirred mixture of 4-methoxy-2-[(phenylsultonyl)methyl]aniline (5.33 g, 19.2 mmol) and para-toluenesulfonic acid (ptsa) monohydrate (0.13 g) in triethyl orthoformate (70 mL) is heated at reflux under nitrogen for 2.5 h, cooled to room temperature, and concentrated in vacuo. The resultant residue is treated with CH₂Cl₂, washed with saturated NaHCO₃, dried over MgSO₄ and concentrated in vacuo to an oil. This oil is stirred in dry THF under nitrogen, treated with 1.0M KOt-Bu in THF (21.0 mL, 21.0 mmol), stirred for 1.25 h, treated with water and 1.0M aqueous hydrochloric acid and extracted with CH₂Cl₂. The combined extracts are dried over MgSO₄ and concentrated in vacuo, then reconcentrated from hexanes to afford a brown solid. Chromatography (ethyl acetate) of the solid gives the title compound as a tan solid, 4.85 g (88% yield), mp 151–155° C., characterized by mass spectral and HNMR analyses.

EXAMPLE 19

Preparation of 2-methyl-3-(phenylsulfonyl)-1H-indole

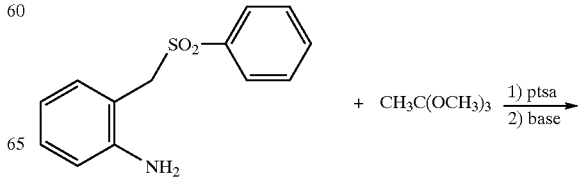

-continued

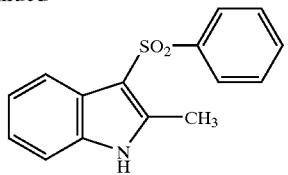

Using essentially the same procedure described in Example 18 hereinabove and employing 2-[(phenylsulfonyl)methyl]aniline and trimethyl orthoacetate as reactants, the title product is obtained as an off-white solid, characterized by mass spectral and HNMR analyses.

EXAMPLES 20–27

Preparation of 1-(Aminoalkyl)-3-(arylsulfonyl)-1H-indole derivatives

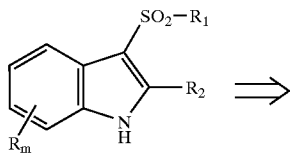

$\Rightarrow$

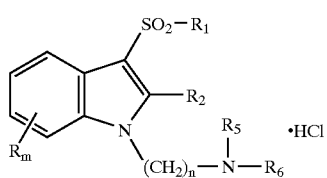

Using essentially the same procedures described in Examples 3 through 19 hereinabove and employing the appropriately substituted arylsulfonylindole substrate and desired amine, the compounds shown in Table II are obtained and identified by mass spectral and HNMR analyses.

EXAMPLE 28

Preparation of Indol-3-ylthiol

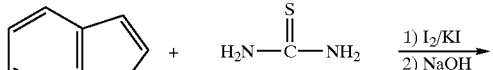

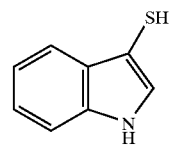

A stirred solution of indole (5.86 g, 50.0 mmol) and thiourea (3.81 g, 50.0 mmol) in methanol is treated with a mixture of iodine (12.70 g, 50.0 mmol) and KI (8.35 g, 50.0 mmol) in water, stirred for 1 h, filtered through a cotton plug, concentrated in vacuo to remove methanol and ⅓ of water, and filtered concentrated solution again. The tan solid filtercake is heated with 2M NaOH at 85° C. for 30 min, cooled and filtered. The filtrate is acidified with conc. HCl to pH1 and filtered. This filtercake is dried under a nitrogen stream to afford the title compound as a cream-colored solid, 4.30 g (58% yield), identified by HNMR analysis.

EXAMPLE 29

Preparation of 3-(Benzylthio)-1H-indole

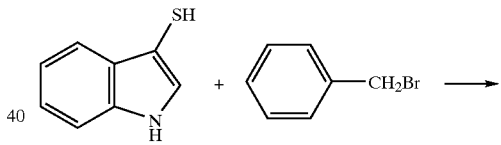

TABLE II

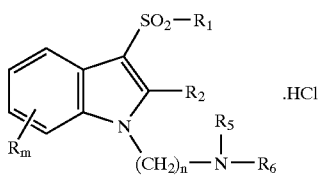

| Ex No | Rm | R1 | R2 | n | R5 | R6 | mp ° C. | % Yield |
|---|---|---|---|---|---|---|---|---|
| 20 | 5-OCH₃ | C₆H₅ | H | 2 | CH₃ | CH₃ | 214–216 | 69ᵃ |
| 21 | 5-OCH₃ | C₆H₅ | H | 2 | H | H | 198–201 | — |
| 22 | 5-OCH₃ | C₆H₅ | H | 2 | CH₂CH₂CH₂CH₂ | | 136–137 | 88ᵃ |
| 23 | 7-OCH₃ | C₆H₅ | H | 2 | CH₃ | CH₃ | 236–238 | 86 |
| 24 | H | C₆H₅ | CH₃ | 2 | CH₃ | CH₃ | 258–260 | 80 |
| 25 | H | 3-F—C₆H₄ | H | 2 | CH₃ | CH₃ | 210–211 | — |
| 26 | H | 1-naphthyl | H | 2 | CH₃ | CH₃ | 239–241 | — |
| 27 | 6-C₆H₅ | C₆H₅ | H | 2 | CH₃ | CH₃ | 253–254 | — |

ᵃFree amine

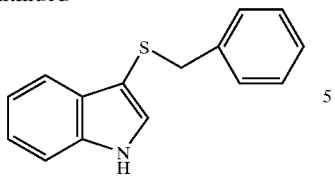

A solution of 3-thio-1H-indole (3.72 g, 25.0 mmol) in dry dioxane under nitrogen is treated with ⅓ portion of total NaH (1.00 g, 25.0 mmol, 60% in oil) followed by benzyl bromide (2.97 mL, 25.0 mmol), held for 3 min, treated with the remaining NaH, stirred for 2.5 h, treated with water and extracted with ether. The combined extracts are washed with brine, dried over MgSO$_4$ and concentrated in vacuo. Chromatography (1:4 ethylacetate:hexane) of the resultant residue gives the title product as a pale yellow solid, 4.75 g (80% yield), mp 84–86° C., identified by mass spectral and HNMR analyses.

EXAMPLE 30

Preparation of 3-(Benzylsulfonyl)-1H-indole

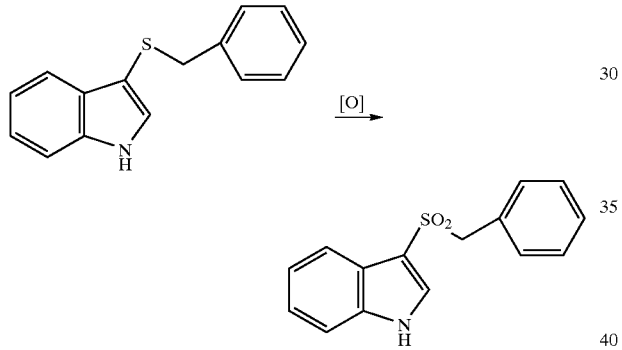

A stirred solution of 3-(benzylthio)-1H-indole (4.62 g, 19.3 mmol) in acetone and 0.2M NaHCO$_3$ is treated with OXON®[1] (29.7 g, 48.3 mmol) over 5 minutes, stirred for 5 h, concentrated in vacuo to remove the acetone and extracted with CH$_2$Cl$_2$. The combined extracts are dried over MgSO$_4$ and concentrated in vacuo. The resulting oil is chromatographed (1:1 ethyl acetate:hexanes) to afford the title compound as a tan solid, 5.11 g (98% yield), mp 153–155° C., identified by mass spectral and HNMR analyses.

[1]2KHSO$_5$.KHSO$_4$.K$_2$SO$_4$, manufactured by DuPont, Wilmington, Del.

EXAMPLES 31–33

Preparation of N-{2-[3-(Benzylsulfonyl)-1H-indol-1-yl]alkyl} amine derivatives

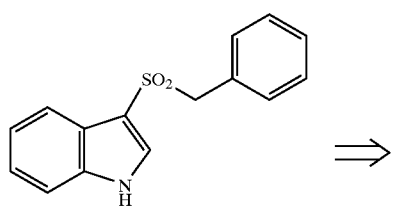

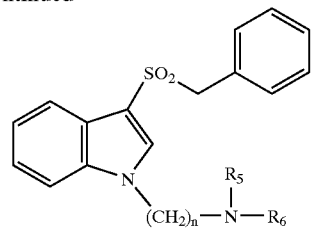

Using essentially the same procedure described in Examples 3 through 5 hereinabove and employing 3-(benzylsulfonyl)-1H-indole as a substrate and the desired amine reagent, the compounds shown on Table III are obtained and identified by mass spectral and HNMR analyses.

TABLE III

| Ex. No. | n | R5 | R6 | mp ° C. | % Yield |
|---|---|---|---|---|---|
| 31 | 2 | CH$_3$ | CH$_3$ | 219–220 | 77 |
| 32 | 2 | CH$_2$—CH$_2$—CH$_2$—CH$_2$—CH$_2$ | | 223–225 | 90 |
| 33 | 3 | H | H | 167–170 | 81 |

EXAMPLE 34

Preparation of 3-(Phenylsulfonyl)-1H-indazole

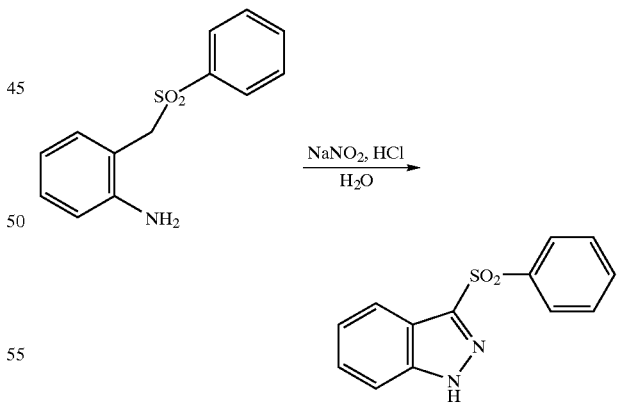

A stirred solution of 2-[(phenylsulfonyl)methyl]aniline (247 mg, 1.00 mmol) in 4N HCl (50 ml) is treated with a solution of NaNO$_2$ (100 mg, 1.5 mmol) in water at ice-bath temperatures, stirred for 30 min., neutralized with 10% NaOH and filtered. The filtercake is dissolved in CH$_2$Cl$_2$, dried over MgSO$_4$ and concentrated in vacuo to afford the title product as a tan solid, 240 mg (93% yield), mp 118° C., identified by mass spectral and HNMR analyses.

EXAMPLE 35

Preparation of N, N-Dimethyl-n-{2-[3-(phenylsulfonyl)-1H-indazol-1-yl]ethyl}amine Hydrochloride

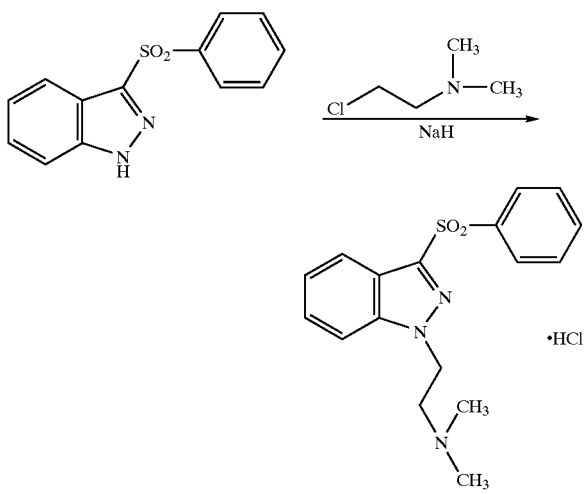

A stirred solution of 3-(phenylsulfonyl)-1H-indazole (210 mg, 0.81 mmol) in anhydrous DMF is treated with 60% NaH in mineral oil (97 mg, 2.44 mmol), stirred for 0.3 h at 20° C., treated with N-(2-chloroethyl)-N,N-dimethyl amine hydrochloride (175 mg, 1.21 mmol), heated at 60° C. for 2 h, quenched with 10% aqueous LiCl and extracted with ether. The combined extracts are washed with brine, dried over $MgSO_4$ and concentrated in vacuo. The resultant residue is chromatographed (1:1 ethanol:ethyl acetate) to give the free amine as a light yellow oil. This oil is dissolved in ethanol, treated with 2N HCl in ether and concentrated in vacuo to give a white solid residue. This residue is triturated in ether and filtered. The filtercake is dried in vacuo to afford the title product as a white solid, 180 mg (60% yield) mp 215° C., identified by mass spectral and HNMR analyses.

EXAMPLES 36 and 37

Preparation 1-(Aminoethyl)-3-(arylsulfonyl)-1H-indazole Derivatives

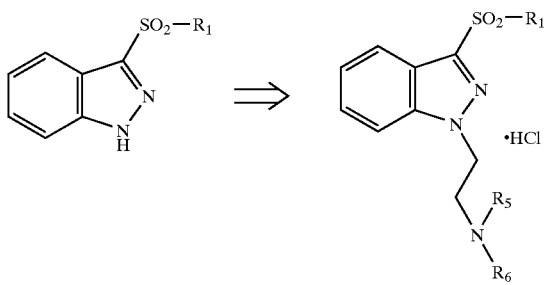

Using essentially the same procedures described in Examples 16, 17, 34 and hereinabove and employing the appropriately substituted sulfonylindazole substrate and the desired haloalkylamine reagent, the compounds shown on Table IV are obtained and identified by mass spectral and HNMR analyses.

TABLE IV

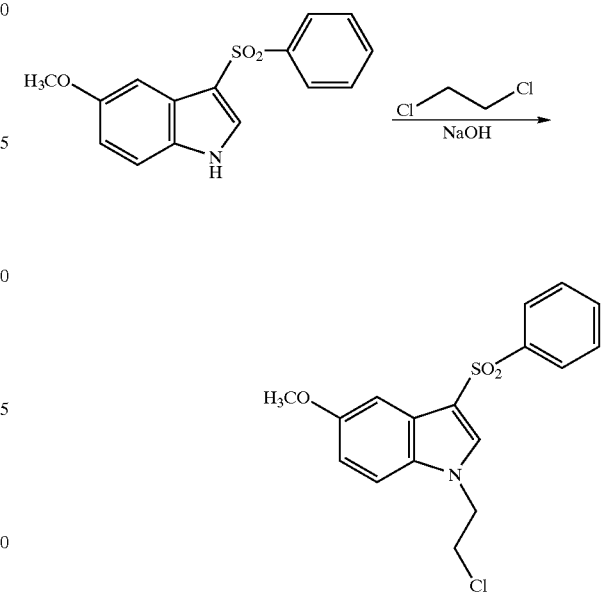

| Ex. No. | R1 | R5 | R6 | mp ° C. |
|---|---|---|---|---|
| 36 | $C_6H_5$ | H | H | 208–209 |
| 37 | 3-F—$C_6H_4$ | $CH_3$ | $CH_3$ | 192–194 |

EXAMPLE 38

Preparation of 1-(2-Chloroethyl)-5-methoxy-3-(phenylsulfonyl)-1H-indole

A mixture of 5-methoxy-3-(phenylsulfonyl)-1H-indole (200 mg, 0.70 mmol), 1,2-dichloroethane (1.3 ml, 16 mmol), 50% aqueous NaOH (84 mg, 1.09mmol NaOH) and tricaprylylmethylammonium chloride (283 mg, 0.70 mmol) is stirred for 3 h at 55° C. and diluted with $CH_2Cl_2$ and water. The phases are separated and the organic phase is dried over $MgSO_4$ and concentrated in vacuo. The resultant residue is chromatographed (80/20 $CH_2Cl2$/hexanes as eluent) to give the title product as a white solid, 153 mg (63% yield), mp 148–150° C., identified by HNMR analysis.

EXAMPLE 39

Preparation of N-Benzyl-N-{2-[5-methoxy-3-(phenylsulfonyl)-1H-indol-1-yl]ethyl}amine

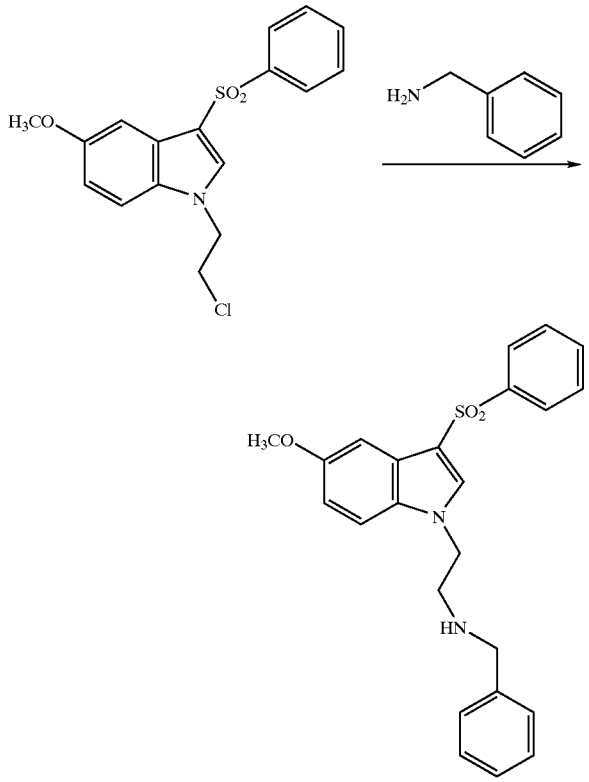

A mixture of 1-(2-chloroethyl)-5-methoxy-3-(phenylsulfonyl)-1H-indole (180mg, 0.51 mmol) and benzylamine (0.89 ml, 8.1 mmol) is heated neat, under $N_2$ at 90° C. for 16 h and dried in vacuo. The resultant residue is partitioned between $CH_2Cl_2$ and saturated $NaHCO_3$. The organic phase is dried over $MgSO_4$ and concentrated in vacuo to give a semi-solid residue. This residue is chromatographed (2% triethylamine in EtOAc as eluent) to give a yellow solid. This solid is recrystallized from ether to afford the title product as a white solid, 163mg (76% yield), mp 98–99° C., identified by HNMR analysis.

EXAMPLES 40–55

Preparation 1-Aminoethyl-3-arylsulfonyl-1H-indole Derivatives

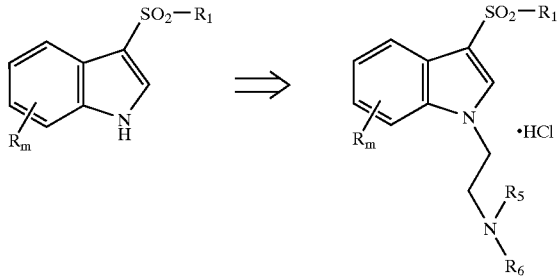

Using essentially the same procedures described in Examples 5, 35, 38 and 39 hereinabove and employing the appropriately substituted sulfonylindole substrate and the desired alkylamine or phthalimide reagent, the compounds shown on Table V are obtained and identified by mass spectral and HNMR analyses. Compounds on Table V, wherein the melting point is recorded with an asterisk, represent the free amine compound.

TABLE V

| Ex. No. | Rm | R1 | R5 | R6 | mp ° C. |
|---|---|---|---|---|---|
| 40 | H | $C_6H_5$ | H | H | 220–221 |
| 41 | 6-$OCH_3$ | $C_6H_5$ | H | H | 236–238 |
| 42 | 5-F | $C_6H_5$ | H | H | 230–231 |
| 43 | 6-$CH_3$ | $C_6H_5$ | H | H | 181–184 |
| 44 | 6-Cl | $C_6H_5$ | H | H | 200–206 |
| 45 | H | 4-$CH_3$—$C_6H_4$ | H | H | 178–183 |
| 46 | H | 1-$CH_3$-imidazo-2-yl | H | H | 158–160 |
| 47 | 5-F | $C_6H_5$ | $CH_3$ | $CH_3$ | 103–104* |
| 48 | 6-$OCH_3$ | $C_6H_5$ | $CH_3$ | $CH_3$ | 121–122* |
| 49 | 6-$CH_3$ | $C_6H_5$ | $CH_3$ | $CH_3$ | 131–132* |
| 50 | 6-F | $C_6H_5$ | $CH_3$ | $CH_3$ | 100–102* |
| 51 | 6-Cl | $C_6H_5$ | $CH_3$ | $CH_3$ | 104–106* |
| 52 | H | 4-$CH_3$—$C_6H_4$ | $CH_3$ | $CH_3$ | >250 |
| 53 | 4-$OCH_3$ | $C_6H_5$ | $CH_3$ | $CH_3$ | 238–240 |
| 54 | 4-CN | $C_6H_5$ | $CH_3$ | $CH_3$ | 260–263 |
| 55 | 6-CN | $C_6H_5$ | $CH_3$ | $CH_3$ | 254–257 |

EXAMPLE 56

Preparation of N,N-Dimethyl-N-[2-(1H-indol-1-yl)ethyl]amine

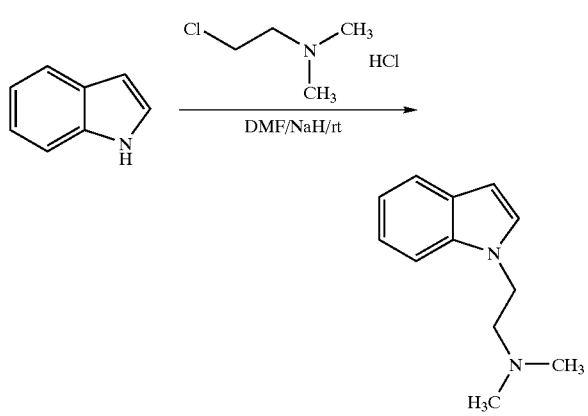

A stirred solution of 1H-indole (1.40 g, 11.95 mmol) in DMF at ambient temperature is treated with 95% NaH in oil (0.900 g, 35.6 mmol). After gas evolution subsides, the reaction mixture is treated with 2-(dimethylamino)ethyl chloride hydrochloride (1.82 g, 12.6 mmol), stirred for 16 h and concentrated in vacuo. The resultant residue is partitioned between ethyl acetate and water. The organic phase is dried over $MgSO_4$ and concentrated in vacuo to afford the title compound as an oil, 1.61 g (72% yield), identified by HNMR and mass spectral analyses.

EXAMPLE 57

Preparation of N,N-Dimethyl-N-[2-(3-{[2-(trifluoromethoxy)phenyl]sulfonyl}-1H-indol-1-yl)ethyl]amine Hydrochloride

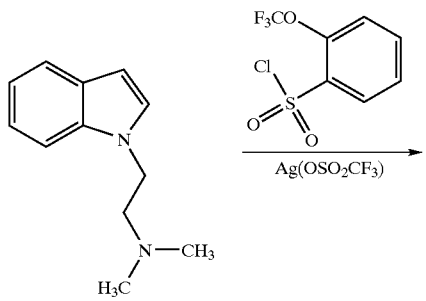

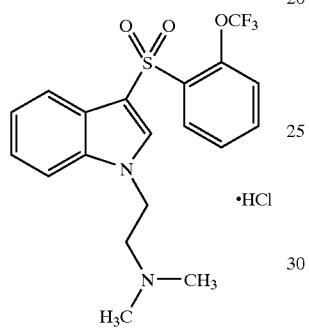

A stirred solution of N,N-dimethyl-N-[2-(1H-indol-1-yl)ethyl]amine (1.88 g, 10.0 mmol) in nitrobenzene is treated with 2-(trifluoromethoxy)phenylsulfonyl chloride (2.87 g, 11.0 mmol) under nitrogen followed by silver trifluoromethanesulfonate (3.35 g, 13.0 mmol), heated to 125° C. for 16 h, cooled and treated with saturated aqueous NaHCO$_3$. The mixture is extracted with CH$_2$Cl$_2$. The extracts are combined, dried over MgSO$_4$ and concentrated in vacuo. The resultant residue is chromatographed eluting with ethanol to give the free amine of the title product. The amine is dissolved in ethanol, treated with 4M HCl in dioxane, stirred for 16 h. and filtered. The filtercake is washed with ether and dried to afford the title compound as a pink solid, mp 198–201° C., identified by mass spectral and HNMR analyses.

EXAMPLES 58 and 59

Preparation of 1-Aminoethyl-3-arylsulfonyl-1H-indole Derivatives

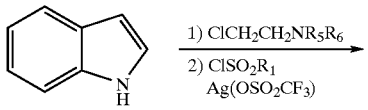

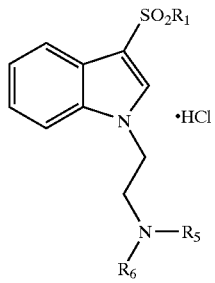

Using essentially the same procedures described in Examples 56 and 57 hereinabove and employing the appropriately substituted 2-chloroethylamine and the desired arylsulfonylchloride reagent, the compounds shown on Table VI are obtained and identified by mass spectral and HNMR analyses.

TABLE VI

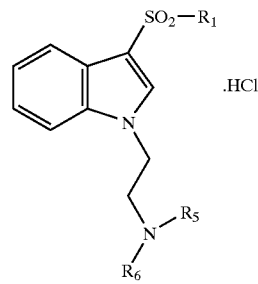

| Ex. No. | R1 | R5 | R6 | mp ° C. |
|---|---|---|---|---|
| 58 | 6-Cl-imidazo[2,1-b][1,3]thiazol-5-yl | CH$_3$ | CH$_3$ | 138–140 |
| 59 | 3-CH$_3$-5-Cl-benzothien-2-yl | CH$_3$ | CH$_3$ | 232–234 |

EXAMPLE 60

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%. Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits.

The amount of displacement by the test compound is given in percent (%) inhibition and is derived from the following equation:

$$\% \text{ inhibition} = \left(1 - \frac{B_0 - NSB}{TB - NSB}\right) 100$$

where $B_0$ is the amount of CPM bound in the presence of the testing agent. NSB represents the CPM bound in the presence of a saturating concentration of a displacer and TB represents the total amount of CPM bound at zero (0) concentration of test compound.

Alternatively, a linear regression line of decline of data points is plotted, from which the $IC_{50}$ value can be read off and the $K_i$ value determined by solving the following equation:

$$K_i = \frac{IC_{50}}{1 + L/K_D}$$

Where L is the concentration of the radioactive ligand used and $K_0$ is the dissociation constant of the ligand for the receptor, both expressed in nM. Using this assay, the % inhibition and $K_i$ values shown in Table VII are obtained.

TABLE VII

| Test Compound (Ex. No.) | 5-HT6 Binding Ki (nM) | % Inhibition at 1 µM |
|---|---|---|
| 3 | 20 | — |
| 5 | 92 | — |
| 6 | — | — |
| 7 | 160 | — |
| 8 | 45 | — |
| 9 | 98 | — |
| 10 | 98 | — |
| 11 | 134 | — |
| 12 | 183 | — |
| 13 | 65 | — |
| 14 | 755 | 35 |
| 15 | 169 | — |
| 20 | 23 | 88 |
| 21 | — | 86 |
| 22 | — | 66 |
| 23 | 25 | — |
| 24 | 18 | — |
| 25 | 13 | — |
| 26 | 4 | — |
| 27 | 23 | — |
| 31 | 1011 | — |
| 32 | 644 | — |
| 33 | — | — |
| 35 | 74 | — |
| 36 | 44 | — |
| 37 | 55 | — |
| 39 | 59 | — |
| 40 | 25 | — |
| 41 | — | 78 |
| 42 | 27 | — |
| 43 | — | 87 |
| 44 | 141 | — |
| 45 | 25 | — |
| 46 | 573 | — |
| 47 | 44 | — |
| 48 | 23 | — |
| 49 | 51 | — |
| 50 | 46 | — |
| 51 | 42 | — |
| 52 | 57 | — |
| 53 | 152 | — |
| 54 | — | 21 |
| 55 | — | 42 |
| 57 | 16 | — |
| 58 | 6 | — |
| 59 | — | 75 |

| Comparative Examples | 5-HT6 Binding Ki (nM) |
|---|---|
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:

1. A compound of formula I

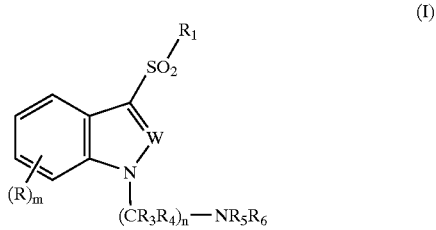

(I)

wherein

W is N or $CR_2$;

R is H, halogen, CN, $OCO_2R_7$, $CO_2R_8$, $CONR_9R_{10}$, $SO_pR_{11}$, $NR_{12}R_{13}$, $OR_{14}$, $COR_{15}$ or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$–$C_6$alkyl, $C_1$–$C_6$alkoxy, $C_3$–$C_7$cycloalkyl, aryl or heteroaryl group each optionally substituted;

$R_3$ and $R_4$ are each independently H or an optionally substituted $C_1$–$C_6$alkyl group;

$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_5$ and $R_6$ may be taken together with the atom to which they are attached to form an optionally substituted 5- to 8-membered ring optionally containing an additional heteroatom selected from O, $NR_{16}$ or $SO_x$;

m is 0 or an integer of 1, 2 or 3;

n is an integer of 2, 3, 4 or 5;

p and x are each independently 0 or an integer of 1 or 2;

$R_7$, $R_8$, $R_{11}$, $R_{15}$ and $R_{16}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or a $C_1$–$C_6$alkyl or $C_3$–$C_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;

$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;

$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

q is 0 or an integer of 1 or 2; and $R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted; or a stereoisomer thereof or a pharmaceutically acceptable salt thereof.

2. The compound according to claim 1 wherein n is 2.

3. The compound according to claim 1 wherein $R_1$ is an optionally substituted phenyl, naphthyl or imidazothiazolyl group.

4. The compound according to claim 1 wherein $R_2$ is H or $CH_3$.

5. The compound according to claim 1 wherein $R_5$ and $R_6$ are each independently H or $C_1$–$C_4$alkyl.

6. The compound according to claim 2 wherein R is H, halogen or $C_1$–$C_4$alkoxy.

7. The compound according to claim 6 wherein $R_3$ and $R_4$ are H.

8. The compound according to claim 7 wherein $R_1$ is an optionally substituted phenyl, naphthyl or imidazothiazolyl group and $R_2$ is H or $CH_3$.

9. The compound according to claim 1 selected from the group consisting of:

2-[5-methoxy-3-(phenylsulfonyl)-1H-indol-1-yl] ethylamine;

6-chloro-1-(3-morpholin-4-yl-propyl)-3-(phenylsulfonyl)-1H-indole;

5-methoxy-3-(phenylsulfonyl)-1-(3-pyrrolidin-1-yl-propyl)-1H-indole;

N,N-dimethyl-N-{3-[3-(4-fluorophenylsulfonyl)-5-methoxy-1H-indol-1-yl]-propyl}-amine;

N,N-dibenzyl-N-{[2-(3-phenylsulfonyl)-1H-indol-1-yl] ethyl}amine;

5-methoxy-3-(phenylsulfonyl)-1-(2-pyrrolidin-1-yl-ethyl)-1H-indole;

N,N-dimethyl-N-{2-[3-(4-fluorophenylsulfonyl)-5-methoxy-1H-indol-1-yl]-ethyl}amine;

N,N-dimethyl-3-[3-(phenylsulfonyl)-1H-indol-1-yl] propan-1-amine;

2-[3-(phenylsulfonyl)-1H-indol-1-yl]ethylamine;

2-[3-(naphth-1-ylsulfonyl)-1H-indol-1-yl]ethylamine;

2-{3-[(6-chloro-imidazo[2,1-b][1,3]thiazol-5-yl) lsulfonyl]-1H-indol-1-yl]ethylamine;

3-[3-(phenylsulfonyl)-1H-indol-1-yl]propan-1-amine;

3-[3-(4-fluorophenylsulfonyl)-5-methoxy-1H-indol-1-yl] propan-1-amine;

3-(phenylsulfonyl)-1-(2-piperidin-1-yl-ethyl)-1H-indole;

3-[5-methoxy-3-(phenylsulfonyl)-1H-indol-1-yl]propan-1-amine;

3-[6-chloro-3-(phenylsulfonyl)-1H-indol-1-yl]propan-1-amine;

6-chloro-1-(2-morpholin-4-yl-ethyl)-3-(phenylsulfonyl)-1H-indole;

3-(phenylsulfonyl)-1-(3-piperidin-1-yl-propyl)-1H-indole;

2-[6-chloro-3-(phenylsulfonyl)-1H-indol-1-yl] ethylamine;

2-[3-(4-fluorophenylsulfonyl)-5-methoxy-1H-indol-1-yl] ethylamine;

N,N-dimethyl-N-{2-[2-methyl-3-(phenylsulfonyl)-1H-indol-1-yl]ethyl}amine;

N,N-dimethyl-N-{2-[5-carbonitrile-3-(phenylsulfonyl)-1H-indol-1-yl]ethyl}amine hydrochloride;

N,N-dimethyl-N-{2-[4-fluoro-3-(phenylsulfonyl)-1H-indol-1-yl]ethyl}amine;

N,N-dimethyl-N-{2-[7-chloro-3-(phenylsulfonyl)-1H-indol-1-yl]-ethyl}amine;

N,N-dimethyl-N-{2-[4-chloro-3-(phenylsulfonyl)-1H-indol-1-yl]-ethyl}amine;

N,N-dimethyl-N-{2-[4-methyl-3-(phenylsulfonyl)-1H-indol-1-yl]ethyl}amine;

N,N-dimethyl-N-{2-[7-ethyl-3-(phenylsulfonyl)-1H-indol-1-yl]ethyl}amine;

N,N-dimethyl-{N-[3-(thien-2ylsulfonyl)-1H-indol-1-yl] ethyl}amine;

2-[3-(thien-2-ylsulfonyl)-1H-indol-1-yl]ethylamine;

1-[2-(dimethylamino)ethyl]-3-(phenylsulfonyl)-1H-indole-5-carbonitrile;

1-[2-(dimethylamino)ethyl]-3-(phenylsulfonyl)-1H-indole-7-carbonitrile;

2-[5-methoxy-3-(phenylsulfonyl)-1H-indazol-1-yl)] ethylamine;

6-chloro-1-(3-morpholin-4-yl-propyl)-3-(phenylsulfonyl)-1H-indazole;

5-methoxy-3-(phenylsulfonyl)-1-(3-pyrrolidin-1-yl-propyl)-1H-indazole;

N,N-dimethyl-N-{3-[3-(4-fluorophenylsulfonyl)-5-methoxy-1H-indazol-1-yl]-propyl}-amine;

N,N-dibenzyl-N-{[2-(3-phenylsulfonyl)-1H-indazol-1-yl]ethyl}amine;

5-methoxy-3-(phenylsulfonyl)-1-(2-pyrrolidin-1-yl-ethyl)-1H-indazole;

N,N-dimethyl-N-3-{2-[3-(4-fluorophenylsulfonyl)-5-methoxy-indazol-1-yl]-ethyl}amine;

N,N-dimethyl-N-3-[3-(phenylsulfonyl)-1H-indazol-1-yl]propan-1-amine;

2-[3-(phenylsulfonyl)-1H-indazol-1-yl]ethylamine;

2-[3-(naphth-1-ylsulfonyl)-1H-indazol-1-yl]ethylamine;

2-{3-[(6-chloro-imidazo[2,1-b][1,3]thiazol-5-yl)lsulfonyl]-1H-indazol-1-yl]ethylamine;

3-[3-(phenylsulfonyl)-1H-indazol-1-yl]propan-1-amine;

3-[3-(4-fluorophenysulfonyl)-5-methoxy-indazol-1-yl]propan-1-amine;

3-(phenylsulfonyl)-1-(2-piperidin-1-yl-ethyl)-1H-indazole;

3-[5-methoxy-3-(phenylsulfonyl)-1H-indazol-1-yl]propan-1-amine;

3-[6-chloro-3-(phenylsulfonyl)-1H-indazol-1-yl]propan-1-amine;

6-chloro-1-(2-morpholin-4-yl-ethyl)-3-(phenylsulfonyl)-1H-indazole;

3-(phenylsulfonyl)-1-(3-piperidin-1-yl-propyl)-1H-indazole;

2-[6-chloro-3-(phenylsulfonyl)-1H-indazol-1-yl]ethylamine;

2-[3-(4-fluorophenylsulfonyl)-5-methoxy-1H-indazol-1-yl]ethylamine;

N,N-dimethyl-N-{2-[2-methyl-3-(phenylsulfonyl)-1H-indazol-1-yl]ethyl}-amine;

N,N-dimethyl-N-{2-[2-methyl-3-(naphth-1-ylsulfonyl)-1H-indazol-1-yl]ethyl}-amine;

N,N-dimethyl-N-{2-[5-carbonitrile-3-(phenylsulfonyl)-1H-indazol-1-yl]ethyl}amine;

N,N-dimethyl-N-{2-[4-fluoro-3-(phenylsulfonyl)-1H-indazol-1-yl]ethyl}amine;

N,N-dimethyl-N-{2-[3-(naphth-1ylsulfonyl)-1H-indazol-1-yl]ethyl}amine;

N,N-dimethyl-N-{2-{[3-(6-chloro-imidazo[1,2-b][1,3]thiazol-5-yl)sulfonyl]-1H-indazol-1-yl}ethyl}amine;

N,N-dimethyl-N-{2-[7-chloro-3-(phenylsulfonyl)-1H-indazol-1-yl]-ethyl}amine;

N,N-dimethyl-N-{2-[4-chloro-3-(phenylsulfonyl)-1H-indazol-1-yl]-ethyl}amine;

N,N-dimethyl-N-{2-[4-methyl-3-(phenylsulfonyl)-1H-indazol-1-yl]ethyl}-amine;

the stereoisomers thereof; and the pharmaceutically acceptable salts thereof.

10. A method for the treatment of a disorder of the central nervous system related to or affected by the 5-HT6 receptor in a patient in need thereof which comprises providing to said patient a therapeutically effective amount of a compound of formula I

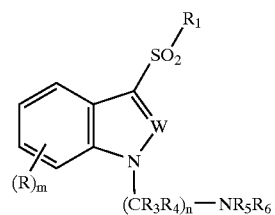

wherein

W is N or $CR_2$;

R is H, halogen, CN, $OCO_2R_7$, $CO_2R_8$, $CONR_9R_{10}$, $SO_pR_{11}$, $NR_{12}R_{13}$, $OR_{14}$, $COR_{15}$ or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$–$C_6$alkyl, $C_1$–$C_6$alkoxy, $C_3$–$C_7$cycloalkyl, aryl or heteroaryl group each optionally substituted;

$R_3$ and $R_4$ are each independently H or an optionally substituted $C_1$–$C_6$alkyl group;

$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_5$ and $R_6$ may be taken together with the atom to which they are attached to form an optionally substituted 5- to 8-membered ring optionally containing an additional heteroatom selected from O, $NR_{16}$ or $SO_x$;

m is 0 or an integer of 1, 2 or 3;

n is an integer of 2, 3, 4 or 5;

p and x are each independently 0 or an integer of 1 or 2;

$R_7$, $R_8$, $R_{11}$, $R_{15}$ and $R_{16}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or a $C_1$–$C_6$alkyl or $C_3$–$C_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;

$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;

$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

q is 0 or an integer of 1 or 2; and $R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted; or the stereoisomers thereof or the pharmaceutically acceptable salts thereof.

11. The method according to claim 10 wherein said disorder is an anxiety disorder or a cognitive disorder.

12. The method according to claim 10 wherein said disorder is a neurodegenerative disorder.

13. The method according to claim 11 wherein said disorder is attention deficit disorder or obsessive compulsive disorder.

14. The method according to claim 12 wherein said disorder is stroke or head trauma.

15. A pharmaceutical composition which comprises a pharmaceutically acceptable carrier and an effective amount of a compound of formula I

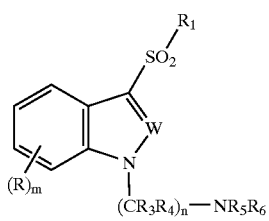

wherein
W is N or $CR_2$;
R is H, halogen, CN, $OCO_2R_7$, $CO_2R_8$, $CONR_9R_{10}$, $SO_pR_{11}$, $NR_{12}R_{13}$, $OR_{14}$, $COR_{15}$ or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

$R_1$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$–$C_6$alkyl, $C_1$–$C_6$alkoxy, $C_3$–$C_7$cycloalkyl, aryl or heteroaryl group each optionally substituted;

$R_3$ and $R_4$ are each independently H or an optionally substituted $C_1$–$C_6$alkyl group;

$R_5$ and $R_6$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted or $R_5$ and $R_6$ may be taken together with the atom to which they are attached to form an optionally substituted 5- to 8-membered ring optionally containing an additional heteroatom selected from O, $NR_{16}$ or $SO_x$;

m is 0 or an integer of 1, 2 or 3;
n is an integer of 2, 3, 4 or 5;
p and x are each independently 0 or an integer of 1 or 2;
$R_7$, $R_8$, $R_{11}$, $R_{15}$ and $R_{16}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_9$ and $R_{10}$ are each independently H or a $C_1$–$C_6$alkyl or $C_3$–$C_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;

$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;

$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

q is 0 or an integer of 1 or 2; and $R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or hetaryl group each optionally substituted; or the stereoisomers thereof or the pharmaceutically acceptable salts thereof.

16. The composition according to claim 15 having the formula I compound wherein n is 2.

17. The composition according to claim 16 having the formula I compound wherein $R_1$ is an optionally substituted phenyl, naphthyl or imidazothiazolyl group.

18. The composition according to claim 17 wherein R is H, halogen or $C_1$–$C_4$alkoxy; $R_2$ is H or $CH_3$, $R_3$ and $R_4$ are H; and $R_5$ and $R_6$ are each independently H or $C_1$–$C_4$alkyl.

19. The composition according to claim 15 having the formula I compound selected from the group consisting of:

2-[5-methoxy-3-(phenylsulfonyl)-1H-indol-1-yl]ethylamine;

6-chloro-1-(3-morpholin-4-yl-propyl)-3-(phenylsulfonyl)-1H-indole;

5-methoxy-3-(phenylsulfonyl)-1-(3-pyrrolidin-1-yl-propyl)-1H-indole;

N,N-dimethyl-N-{3-[3-(4-fluorophenylsulfonyl)-5-methoxy-1H-indol-1-yl]-propyl}-amine;

N,N-dibenzyl-N-{[2-(3-phenylsulfonyl)-1H-indol-1-yl]ethyl}amine;

5-methoxy-3-(phenylsulfonyl)-1-(2-pyrrolidin-1-yl-ethyl)-1H-indole;

N,N-dimethyl-N-{2-[3-(4-fluorophenylsulfonyl)-5-methoxy-1H-indol-1-yl]-ethyl}amine;

N,N-dimethyl-3-[3-(phenylsulfonyl)-1H-indol-1-yl]propan-1-amine;

2-[3-(phenylsulfonyl)-1H-indol-1-yl]ethylamine;

2-[3-(naphth-1-ylsulfonyl)-1H-indol-1-yl]ethylamine;

2-{3-[(6-chloro-imidazo[2,1-b][1,3]thiazol-5-yl)lsulfonyl]-1H-indol-1-yl]ethyl}amine;

3-[3-(phenylsulfonyl)-1H-indol-1-yl]propan-1-amine;

3-[3-(4-fluorophenylsulfonyl)-5-methoxy-1H-indol-1-yl]propan-1-amine;

3-(phenylsulfonyl)-1-(2-piperidin-1-yl-ethyl)-1H-indole;

3-[5-methoxy-3-(phenylsulfonyl)-1H-indol-1-yl]propan-1-amine;

3-[6-chloro-3-(phenylsulfonyl)-1H-indol-1-yl]propan-1-amine;

6-chloro-1-(2-morpholin-4-yl-ethyl)-3-(phenylsulfonyl)-1H-indole;

3-(phenylsulfonyl)-1-(3-piperidin-1-yl-propyl)-1H-indole;

2-[6-chloro-3-(phenylsulfonyl)-1H-indol-1-yl]ethylamine;

2-[3-(4-fluorophenylsulfonyl)-5-methoxy-1H-indol-1-yl]ethylamine;

N,N-dimethyl-N-{2-[2-methyl-3-(phenylsulfonyl)-1H-indol-1-yl]ethyl}amine;

N,N-dimethyl-N-{2-[5-carbonitrile-3-(phenylsulfonyl)-1H-indol-1-yl]ethyl}amine hydrochloride;

N,N-dimethyl-N-{2-[4-fluoro-3-(phenylsulfonyl)-1H-indol-1-yl]ethyl}amine;
N,N-dimethyl-N-{2-[7-chloro-3-(phenylsulfonyl)-1H-indol-1-yl]-ethyl}amine;
N,N-dimethyl-N-{2-[4-chloro-3-(phenylsulfonyl)-1H-indol-1-yl]-ethyl}amine;
N,N-dimethyl-N-{2-[4-methyl-3-(phenylsulfonyl)-1H-indol-1-yl]ethyl}amine;
N,N-dimethyl-N-{2-[7-ethyl-3-(phenylsulfonyl)-1H-indol-1-yl]ethyl}amine;
N,N-dimethyl-{N-[3-(thien-2ylsulfonyl)-1H-indol-1-yl] ethyl}amine;
2-[3-(thien-2-ylsulfonyl)-1H-indol-1-yl]ethylamine;
1-[2-(dimethylamino)ethyl]-3-(phenylsulfonyl)-1H-indole-5-carbonitrile;
1-[2-(dimethylamino)ethyl]-3-(phenylsulfonyl)-1H-indole-7-carbonitrile;
2-[5-methoxy-3-(phenylsulfonyl)-1H-indazol-1-yl)]ethylamine;
6-chloro-1-(3-morpholin-4-yl-propyl)-3-(phenyl-sulfonyl)-1H-indazole;
5-methoxy-3-(phenylsulfonyl)-1-(3-pyrrolidin-1-yl-propyl)-1H-indazole;
N,N-dimethyl-N-{3-[3-(4-fluorophenylsulfonyl)-5-methoxy-1H-indazol-1-yl]-propyl}-amine;
N,N-dibenzyl-N-([2-(3-phenylsulfonyl)-1H-indazol-1-yl]ethyl}amine;
5-methoxy-3-(phenylsulfonyl)-1-(2-pyrrolidin-1-yl-ethyl)-1H-indazole;
N,N-dimethyl-N-3-{2-[3-(4-fluorophenylsulfonyl)-5-methoxy-indazol-1-yl]-ethyl}amine;
N,N-dimethyl-N-3-[3-(phenylsulfonyl)-1H-indazol-1-yl]propan-1-amine;
2-[3-(phenylsulfonyl)-1H-indazol-1-yl]ethylamine;
2-[3-(naphth-1-ylsulfonyl)-1H-indazol-1-yl]ethylamine;
2-{3-[(6-chloro-imidazo[2, 1-b][1,3]thiazol-5-yl)lsulfonyl]-1H-indazol-1-yl]ethylamine;
3-[3-(phenylsulfonyl)-1H-indazol-1-yl]propan-1-amine;
3-[3-(4-fluorophenylsulfonyl)-5-methoxy-indazol-1-yl] propan-1-amine;
3-(phenylsulfonyl)-1-(2-piperidin-1-yl-ethyl)-1H-indazole;
3-[5-methoxy-3-(phenylsulfonyl)-1H-indazol-1-yl] propan-1-amine;
3-[6-chloro-3-(phenylsulfonyl)-1H-indazol-1-yl]propan-1-amine;
6-chloro-1-(2-morpholin-4-yl-ethyl)-3-(phenylsulfonyl)-1H-indazole;
3-(phenylsulfonyl)-1-(3-piperidin-1-yl-propyl)-1H-indazole;
2-[6-chloro-3-(phenylsulfonyl)-1H-indazol-1-yl] ethylamine;
2-[3-(4-fluorophenylsulfonyl)-5-methoxy-1H-indazol-1-yl]ethylamine;
N,N-dimethyl-N-{2-[2-methyl-3-(phenylsulfonyl)-1H-indazol-1-yl]ethyl}-amine;
N,N-dimethyl-N-{2-[2-methyl-3-(naphth-1-ylsulfonyl)-1H-indazol-1-yl]ethyl}-amine;
N,N-dimethyl-N-{2-[5-carbonitrile-3-(phenylsulfonyl)-1H-indazol-1-yl]ethyl}amine;
N,N-dimethyl-N-{2-[4-fluoro-3-(phenylsulfonyl)-1H-indazol-1-yl]ethyl}amine;
N,N-dimethyl-N-{2-[3-(naphth-1-ylsulfonyl)-1H-indazol-1-yl]ethyl}amine;
N,N-dimethyl-N-(2-{[3-(6-chloro-imidazo[1,2-b][1,3]thiazol-5-yl)sulfonyl]-1H-indazol-1-yl}ethyl}amine;
N,N-dimethyl-N-{2-[7-chloro-3-(phenylsulfonyl)-1H-indazol-1-yl]-ethyl}amine;
N,N-dimethyl-N-{2-[4-chloro-3-(phenylsulfonyl)-1H-indazol-1-yl]-ethyl}amine;
N,N-dimethyl-N-{2-[4-methyl-3-(phenylsulfonyl)-1H-indazol-1-yl]ethyl}-amine;
the stereoisomers thereof; and
the pharmaceutically acceptable salts thereof.

20. A process for the preparation of a compound of formula I

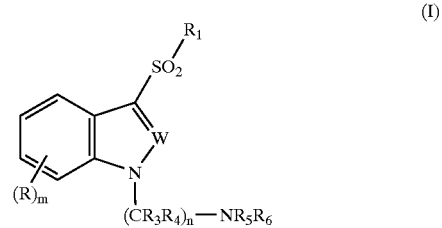

wherein
W is N or CR$_2$;
R is H, halogen, CN, OCO$_2$R$_7$, CO$_2$R$_8$, CONR$_9$R$_{10}$, SO$_p$R$_{11}$, NR$_{12}$R$_{13}$, OR$_{14}$, COR$_{15}$ or a C$_1$–C$_6$alkyl, C$_2$–C$_6$alkenyl, C$_2$–C$_6$alkynyl, C$_3$–C$_7$cycloalkyl, cycloheteroalkyl, aryl or heteroaryl group each optionally substituted;
R$_1$ is an optionally substituted C$_1$–C$_6$alkyl, C$_3$–C$_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;
R$_2$ is H, halogen, or a C$_1$–C$_6$alkyl, C$_1$–C$_6$alkoxy, C$_3$–C$_7$cycloalkyl, aryl or heteroaryl group each optionally substituted;
R$_3$ and R$_4$ are each independently H or an optionally substituted C$_1$–C$_6$alkyl group;
R$_5$ and R$_6$ are each independently H or a C$_1$–C$_6$alkyl, C$_2$–C$_6$alkenyl, C$_2$–C$_6$alkynyl, C$_3$–C$_7$cycloalkyl, cycloheteroalkyl, aryl or heteroaryl group each optionally substituted or R$_5$ and R$_6$ may be taken together with the atom to which they are attached to form an optionally substituted 5- to 8-membered ring optionally containing an additional heteroatom selected from O, NR$_{16}$ or SO$_x$;
m is 0 or an integer of 1, 2 or 3;
n is an integer of 2, 3, 4 or 5;
p and x are each independently 0 or an integer of 1 or 2;
R$_7$, R$_8$, R$_{11}$, R$_{15}$ and R$_{16}$ are each independently H or a C$_1$–C$_6$alkyl, C$_2$–C$_6$alkenyl, C$_2$–C$_6$alkynyl, C$_3$–C$_6$cycloalkyl, cycloheteroalkyl, aryl or heteroaryl group each optionally substituted;
R$_9$ and R$_{10}$ are each independently H or a C$_1$–C$_6$alkyl or C$_3$–C$_7$cycloalkyl group each optionally substituted or $R_9$ and $R_{10}$ may be taken together with the atom to which they are attached to form a 5- to 7-membered ring optionally containing another heteroatom selected from O, $NR_{18}$ or S;

$R_{12}$ and $R_{13}$ are each independently H or an optionally substituted $C_1$–$C_4$alkyl group or $R_{12}$ and $R_{13}$ may be taken together with the atom to which they are attached to form a 5- to 7-membered ring optionally containing another heteroatom selected from O, $NR_{17}$ or $SO_q$;

$R_{14}$ is a $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl group each optionally substituted;

q is 0 or an integer of 1 or 2; and $R_{17}$ and $R_{18}$ are each independently H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted; or which process comprises reacting a compound of formula II

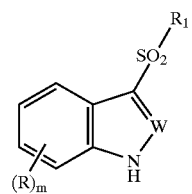

(II)

wherein W, R, $R_1$ and m are as defined hereinabove with a haloalkylamine of formula III

(III)

wherein Hal is Cl, Br or I and $R_3$, $R_4$, $R_5$, $R_6$ and n are as defined hereinabove in the presence of a base optionally in the presence of a solvent.

* * * * *